(12) United States Patent
Luque Vera et al.

(10) Patent No.: US 12,263,281 B2
(45) Date of Patent: Apr. 1, 2025

(54) DEVICE FOR EVAPORATING VOLATILE SUBSTANCES

(71) Applicant: Zobele Holding SPA, Trento (IT)

(72) Inventors: Sergio Luque Vera, Barcelona (ES); Roberto Camarero Díez, Barcelona (ES); Jordi Masó Sabaté, Barcelona (ES); Julio Cesar Ruiz Ballesteros, Barcelona (ES)

(73) Assignee: Zobele Holding SPA, Trento (IT)

( * ) Notice: Subject to any disclaimer, the term of this patent is extended or adjusted under 35 U.S.C. 154(b) by 892 days.

(21) Appl. No.: 16/972,481

(22) PCT Filed: Jun. 7, 2019

(86) PCT No.: PCT/EP2019/064964
§ 371 (c)(1),
(2) Date: Dec. 4, 2020

(87) PCT Pub. No.: WO2019/234226
PCT Pub. Date: Dec. 12, 2019

(65) Prior Publication Data
US 2021/0162087 A1 Jun. 3, 2021

(30) Foreign Application Priority Data
Jun. 7, 2018 (ES) .................. P201830554

(51) Int. Cl.
*A61L 9/03* (2006.01)
*H05B 1/02* (2006.01)
*H05B 3/00* (2006.01)

(52) U.S. Cl.
CPC ............... *A61L 9/037* (2013.01); *H05B 1/02* (2013.01); *H05B 3/0014* (2013.01); *A61L 2209/111* (2013.01); *H05B 2203/021* (2013.01)

(58) Field of Classification Search
CPC ...................................................... A61L 9/037
See application file for complete search history.

(56) References Cited

U.S. PATENT DOCUMENTS 3,564,114 A * 2/1971 Blinder ............... H05K 1/0292
174/254
6,123,935 A 9/2000 Wefler et al.
(Continued)

FOREIGN PATENT DOCUMENTS

EP 0689766 1/1996
EP 1714662 10/2006
(Continued)

OTHER PUBLICATIONS

International Search Report from co-pending PCT App No. PCT/EP2019/064964, filed Jun. 7, 2019.

*Primary Examiner* — Donald R Spamer
(74) *Attorney, Agent, or Firm* — Sandberg Phoenix & von Gontard, P.C.

(57) ABSTRACT

The device for evaporating volatile substances comprises a heater (1) which heats a wick (2) impregnated in said volatile substances and characterised in that said heater (1) is formed from a printed circuit board (10) provided with at least one resistor (11).
It allows a device for evaporating volatile substances to be provided which comprises a heater with a very low thermal mass which allows a rapid increase in the temperature and variation of the working cycles.

20 Claims, 3 Drawing Sheets

(56) References Cited

U.S. PATENT DOCUMENTS

| | | | |
|---|---|---|---|
| 2004/0028551 A1* | 2/2004 | Kvietok | A61L 9/122 422/123 |
| 2004/0145067 A1 | 7/2004 | Millan | |
| 2013/0306752 A1 | 11/2013 | Ruis Ballesteros et al. | |
| 2014/0064714 A1* | 3/2014 | Ques Ramos | A61L 9/037 392/390 |
| 2014/0093224 A1* | 4/2014 | Deflorian | A01M 1/2077 392/395 |

FOREIGN PATENT DOCUMENTS

| | | |
|---|---|---|
| GB | 2449703 | 12/2008 |
| WO | WO03103387 | 12/2003 |
| WO | WO2012171869 | 12/2012 |

\* cited by examiner

DEVICE FOR EVAPORATING VOLATILE SUBSTANCES

The present invention relates to a device for evaporating volatile substances which allows a rapid increase in the temperature and variation of the working cycles.

BACKGROUND OF THE INVENTION

Electric heaters with heated resistors have been widely used for decades in industry to evaporate fragrances and insecticides. There are various solutions adopted to convert the electric current into heat: ceramic heaters, metallic resistors, PTC, etc., the majority of the successful products on the market being based on a heater with an alternating current which has a relevant thermal mass, producing, as a result, a slow evaporation of the volatile substances into the air when it is switched on for the first time.

There are also solutions based on temperature acceleration which require a direct current power source requiring a battery capacitor or an AC/DC power source which represents a substantial increase in the cost of the product in comparison to the systems powered by direct current.

The solutions existing at present have a series of drawbacks, such as:

The low-cost alternating current heaters require a certain time to reach the working temperature which is transferred to the wick impregnated for the diffusion of the volatile substances. The user will wait a long time to notice the smell.

Additionally, when a direct current power source is required, this involves a greater cost for the final solution.

On the other hand, one of the most common problems in all these alternating current devices is the habituation to the fragrances due to the lack of automatic regulation of the device. Due to the constant release of fragrances, the users become accustomed.

In addition, the impregnated wicks used at present are mainly a cylindrical shape which means that they are not well optimised in terms of heat transfer from the heat source.

Another drawback of the devices known at present is the regulation of the diffusion of volatile substances since the existing devices are generally regulated by mechanical regulation which require manual interaction from the user or costly electronic regulation.

Therefore, an object of the present invention is to provide a device for evaporating volatile substances comprising a heater with a very low thermal mass which allows a rapid increase in the temperature and variation of the working cycles.

DESCRIPTION OF THE INVENTION

The cited drawbacks are resolved using the device for evaporating volatile substances, presenting other advantages which will be described below.

The device for evaporating volatile substances according to the present invention comprises a heater which heats a wick impregnated with said volatile substances and is characterised in that said heater is formed from a printed circuit board provided with at least one resistor.

Advantageously, said printed circuit board can also have one or several copper areas to increase the temperature.

To ensure the correct placement of the wick with respect to the heater, said printed circuit board comprises grooves for the passage of stops, the heater is joined to the wick by means of a support and said stops meet with said support, aligning the heater with the wick.

In order to improve evaporation of the volatile substances, said wick is flat.

In addition, the device for evaporating volatile substances according to the present invention also comprises a recipient with liquid with said volatile substances, said liquid impregnating the wick.

If desired, the device for evaporating volatile substances according to the present invention also comprises one or more sensors connected to the printed circuit board, such as a temperature, pressure, motion and/or presence sensor.

Advantageously, said printed circuit board is connected to an alternating current electric power network and to a microcontroller and/or to a switch which allows the working cycles to be controlled.

At least the following advantages are achieved with the device for evaporating volatile substances according to the present invention:

The heater has a very low thermal mass which allows rapid acceleration of the temperature of the wick.

The need for a direct current source for the heater is eliminated, making the device cheaper.

It provides cycles of high/low fragrance intensity, preventing the habituation of the users.

The heat emission area of the wick is optimised owing to its flat shape of the impregnated surface of the wick, allowing the most suitable evaporation of volatile substances to the air, with the minimum use of materials.

BRIEF DESCRIPTION OF THE DRAWINGS

To better understand the foregoing, a set of drawings is accompanied in which a practical embodiment is represented schematically and only by way of non-limiting example.

DESCRIPTION OF A PREFERRED EMBODIMENT

Figure 1:
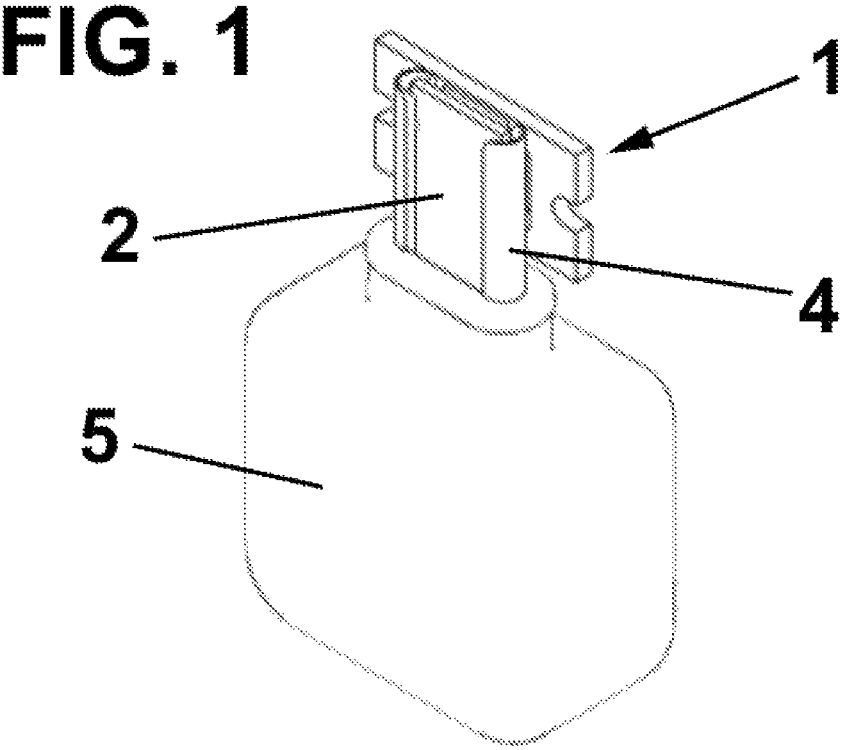
FIG. 1 is a perspective view of the device for evaporating volatile substances according to the present invention without its exterior casing.
Figure 2:
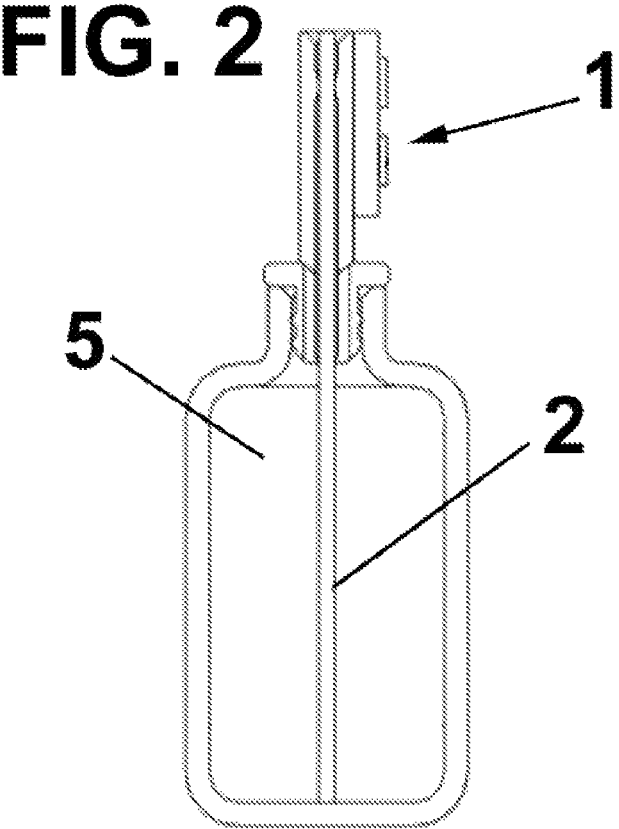
FIG. 2 is a sectional elevation view of the device for evaporating volatile substances of FIG. 1.

As is shown in FIGS. 1 and 2, the device for evaporating volatile substances comprises a heater 1 which heats a wick 2, causing the evaporation of the volatile substances.

One part of the wick 2 is placed in the interior of a recipient 5 containing a liquid with the volatile substances such that said liquid impregnates the wick 2 for the evaporation of the volatile substances when heated by means of the heater 1.

Figure 5:
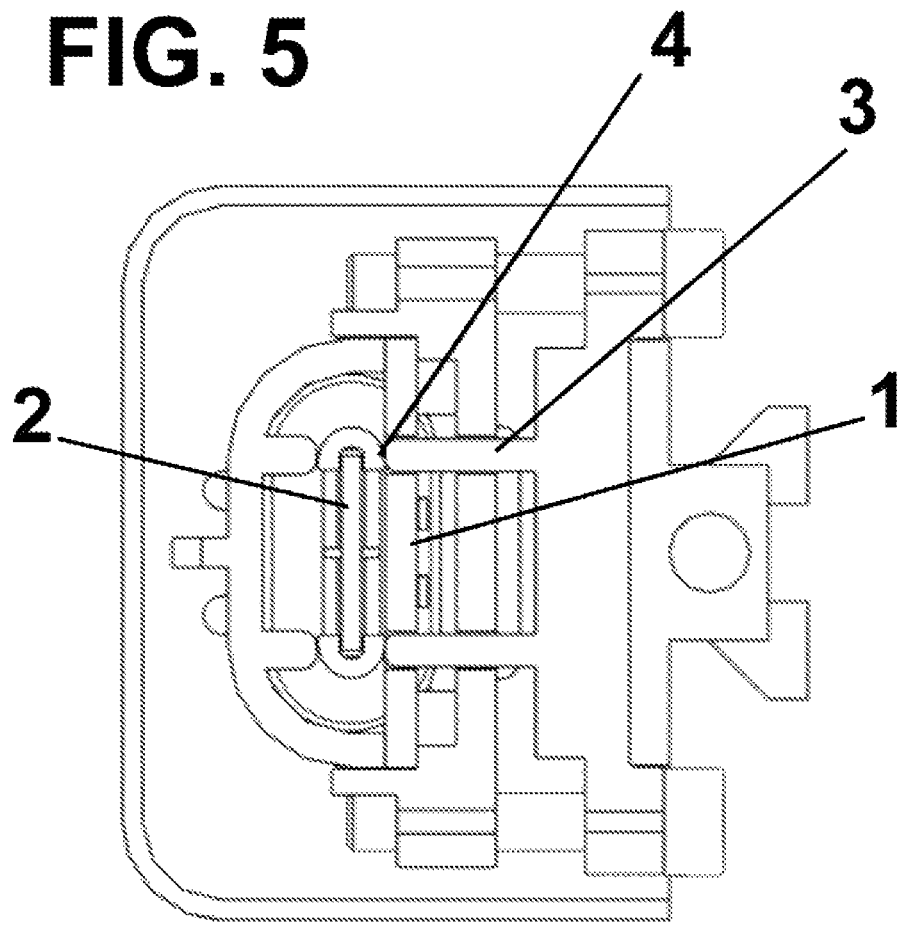
FIG. 5 is a plan view of the device for evaporating volatile substances according to the present invention with its exterior casing, wherein the stops are shown in contact with the support of the wick.

The wick 2 is flat and thin for transporting the liquid which is evaporated in the air by capillary action. The wick has both sides exposed to allow the evaporation of the volatile substances from any side. As shown in FIG. 5, at least one side surface of the wick 2 is exposed to and positioned directly opposite the heater 1 and in particular, at least one side surface of the wick 2 is exposed to and positioned directly opposite the resistor 11 on the at least one side of the printed circuit board 10.

Figure 3:
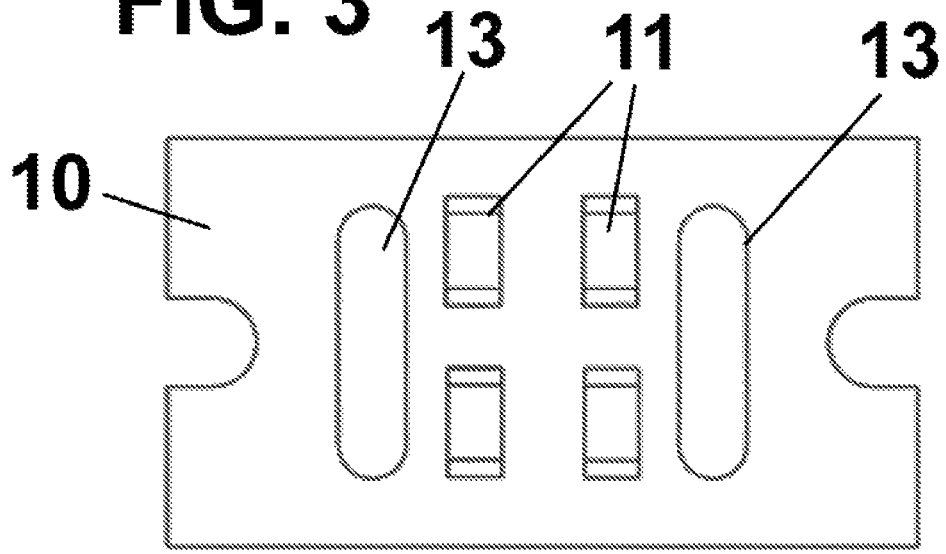
FIGS. 3 and 4 are front and rear views of the printed circuit board of the heater of the device for evaporating volatile substances according to the present invention.
Figure 4:
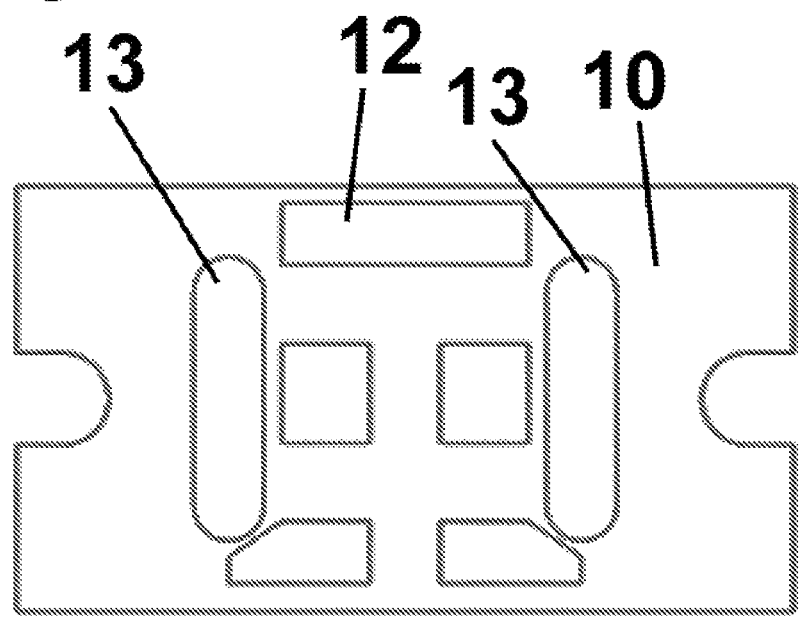

As can be seen in greater detail in FIGS. 3 and 4, the heater 1 is formed from a printed circuit board 10 which is connected to an alternating current electric power source and comprises at least one resistor 11 and can have one or several copper areas.

As is seen in these figures, the resistors 11 are arranged on the face oriented towards the wick 2, while the copper areas 12 are arranged on the opposing face.

This printed circuit board 10 also comprises temperature control means, such as a switch and/or a microcontroller, connected to an alternating/direct current power source without a transformer to control the heating service cycles.

These heating cycles allow a rapid acceleration of the temperature in the impregnated wick, from the inactive state, for more rapid evaporation of the volatile substances and to prevent the habituation to the fragrances of the volatile substances.

If desired, the printed circuit board 10 could comprise at least one sensor to detect various aspects such as the presence of the wick 2, the temperature, light, a printed barcode or any other identification by optical means or another type.

To ensure the correct placement of the wick 2 with respect to the heater 1, the wick 2 is mounted in a support 4 which, in the represented embodiment, is formed by two pieces with U-shaped section.

In turn, the printed circuit board 10 comprises grooves 13 for the placement of stops 3 which, in the assembled position, are in contact with the support 4 of the wick 2, as can be seen in FIG. 5.

The functioning of the device for evaporating volatile substances according to the present invention is the following:

When a user wishes to use the evaporation device, they should connect it to the power source, such as the conventional power network, for example by means of a plug of the device itself which is not shown in the figures.

Owing to the presence of the resistors 11 on the printed circuit board 10, the heater is rapidly heated to heat the part of the wick 2 with respect to said resistors 11 and cause the evaporation of the volatile substances.

Additionally, the user can control the working cycles of the evaporation device by means of the controller of the printed circuit board 10 or equally, to prevent the user from becoming habituated to the fragrance of said volatile substances.

In spite of the fact that reference has been made to a specific embodiment of the invention, it is evident to a person skilled in the art that the device for evaporating volatile substances described is capable of having numerous variations and modifications and that all the details mentioned can be substituted for others which are technically equivalent without departing from the scope of protection defined by the enclosed claims.

The invention claimed is:

1. A device for evaporating volatile substances comprising:
    a heater which heats a wick impregnated in said volatile substances, wherein said heater is formed from a printed circuit board provided with at least one resistor;
    the wick is flat, the wick has opposite sides with both sides of the wick exposed to allow evaporation of the volatile substances into air by capillary action, the wick has a heat emission area that is optimized by a flat shape of an impregnated surface of the wick that allows evaporation of volatile substances to the air;
    the at least one resistor is arranged on a face of the printed circuit board that is oriented toward the exposed heat emission area of the flat shape of the impregnated surface of the wick;
    the wick is mounted in U-shaped sections of a support; and
    said printed circuit board comprises grooves for the passage of stops, in an assembled position the stops are in placement in the grooves of the printed circuit board and in contact with the U-shaped sections of the support.

2. The device for evaporating volatile substances according to claim 1, wherein:
    said printed circuit board also comprises a copper area arranged on a face of the printed circuit board opposite the face of the printed circuit board that is oriented toward the wick.

3. The device for evaporating volatile substances according to claim 1, wherein:
    the heater is joined to the wick by means of the stops placed in the grooves and in contact with the support.

4. The device for evaporating volatile substances according to claim 3, wherein:
    said stops meet with said support, aligning the heater with the wick.

5. The device for evaporating volatile substances according to claim 1, wherein:
    said wick is flat and thin and has opposite sides that are both exposed to air to allow evaporation of the volatile substances into the air from both sides.

6. The device for evaporating volatile substances according to claim 1, wherein:
    the device further comprises a recipient with liquid with said volatile substances, said wick is placed in an interior of the recipient with the liquid impregnating the wick.

7. The device for evaporating volatile substances according to claim 1, wherein:
    the device further comprises one or more sensors connected to the printed circuit board.

8. The device for evaporating volatile substances according to claim 7, wherein:
    one of the said one or more sensors is a temperature, pressure, motion or presence sensor.

9. The device for evaporating volatile substances according to claim 1, wherein:
    said printed circuit board is connected to an alternating current electric power source.

10. The device for evaporating volatile substances according to claim 1, wherein:
    said printed circuit board is connected to a microcontroller, a switch or both a microcontroller and a switch.

11. A device for evaporating volatile substances comprising:
    a heater which heats a wick impregnated with volatile substances, the heater is formed from a printed circuit board having at least one resistor on the printed circuit board;
    the wick is flat and has opposite side surfaces that are flat surfaces and are exposed to air to allow evaporation of the volatile substances from the side surfaces into the air by capillary action;
    the at least one resistor is positioned on a face of the printed circuit board that is oriented toward a side surface of the wick with the side surface of the wick being exposed to the air and exposed to and positioned directly opposite the resistor on the printed circuit board;

the wick is mounted between two sections of a support;

the printed circuit board has grooves configured for the passage of stops through the grooves; and the wick and the printed circuit board are assembled together with the stops placed through the grooves and in contact with the two sections of the support.

12. The device for evaporating volatile substances of claim 11, further comprising:

the printed circuit board having a copper area on a face of the printed circuit board that is on an opposite side of the printed circuit board from the at least one resistor.

13. The device for evaporating volatile substances of claim 10, further comprising:

the heater is joined to the wick by the stops placed through the grooves and in contact with the support.

14. The device for evaporating volatile substances of claim 13, further comprising:

the stops contacting the support align the heater with the wick.

15. The device for evaporating volatile substances of claim 11, further comprising:

the wick is flat and thin and has opposite sides that are directly exposed to air and allow evaporation of volatile substances directly into the air from the opposite sides.

16. The device for evaporating volatile substances of claim 11, further comprising:

the wick is positioned inside a recipient container of a liquid impregnating the wick.

17. The device for evaporating volatile substances of claim 11, further comprising:

sensors connected to the printed circuit board.

18. The device for evaporating volatile substances of claim 17, further comprising:

one of the sensors is a temperature sensor, a pressure sensor, a motion sensor or presence sensor.

19. The device for evaporating volatile substances of claim 11, further comprising:

the printed circuit board is connected to an alternating current electric power source.

20. The device for evaporating volatile substances of claim 11, further comprising:

the printed circuit board is connected to a microcontroller, a switch or both a microcontroller and a switch.

* * * * *